United States Patent
Hossack

[19]

[11] Patent Number: 5,957,851
[45] Date of Patent: Sep. 28, 1999

[54] EXTENDED BANDWIDTH ULTRASONIC TRANSDUCER

[75] Inventor: John Hossack, Palo Alto, Calif.

[73] Assignee: Acuson Corporation, Mountain View, Calif.

[21] Appl. No.: 09/129,181

[22] Filed: May 5, 1998

Related U.S. Application Data

[63] Continuation of application No. 08/661,227, Jun. 10, 1996.

[51] Int. Cl.⁶ ..................................................... A61B 8/00
[52] U.S. Cl. .......................................................... 600/459
[58] Field of Search .................................. 600/447, 459, 600/463, 472, 443, 466, 449

[56] References Cited

U.S. PATENT DOCUMENTS

| | | |
|---|---|---|
| 4,096,756 | 6/1978 | Alphonse . |
| 4,240,003 | 12/1980 | Larson, III . |
| 4,276,491 | 6/1981 | Daniel . |
| 4,354,132 | 10/1982 | Borburgh et al. . |
| 4,356,422 | 10/1982 | Van Maanen . |
| 4,427,912 | 1/1984 | Bui et al. . |
| 4,446,739 | 5/1984 | Coursant . |
| 4,550,607 | 11/1985 | Maslak et al. . |
| 4,712,037 | 12/1987 | Verbeek et al. . |
| 4,735,096 | 4/1988 | Dorr . |
| 4,736,631 | 4/1988 | Takeuchi et al. . |
| 5,115,809 | 5/1992 | Saitoh et al. . |
| 5,158,071 | 10/1992 | Umemura et al. ...................... 600/443 |
| 5,163,436 | 11/1992 | Saitoh et al. . |
| 5,305,756 | 4/1994 | Entrekin et al. . |
| 5,345,139 | 9/1994 | Gururaja et al. . |
| 5,381,067 | 1/1995 | Greenstein et al. . |
| 5,389,848 | 2/1995 | Trzaskos . |
| 5,396,143 | 3/1995 | Seyed-Bolorforosh et al. . |
| 5,410,205 | 4/1995 | Gururaja . |
| 5,410,516 | 4/1995 | Uhlendorf et al. . |
| 5,415,175 | 5/1995 | Hanafy et al. . |
| 5,423,220 | 6/1995 | Finsterwald et al. . |
| 5,435,311 | 7/1995 | Umemura et al. ...................... 600/443 |
| 5,438,554 | 8/1995 | Seyed-Bolorforosh et al. . |
| 5,438,998 | 8/1995 | Hanafy . |
| 5,446,333 | 8/1995 | Ishida et al. . |
| 5,724,976 | 3/1998 | Mine et al. . |

FOREIGN PATENT DOCUMENTS

WO 94/16826  8/1994  WIPO .

OTHER PUBLICATIONS

Sittig, E., "Transmission Parameters of Thickness–Driven Piezoelectric Transducers Arranged in Multilayer Configurations," IEEE Transactions on Sonics and Ultrasoncis, vol. SU–14, No. 4, Oct. 1967, pp. 167–174.

Burckhardt, C.B., "Ultrasound Axicon: a device for focusing over a large depth," E. Hoffman–La Roche & Company, vol. 54, No. 6, 1973, pp. 1628–1630.

Yamada, K. et al., "Conical and Toroidal Piezoelectric Polymer Transducers for Long Range Focusing," Ultrasonics Symposium, 1982, pp. 837–840.

"Apodized Conical Focusing for Ultrasound Imaging," IEEE Transactions on Sonics and Ultrasonics, vol. SU–29, No. 3, May 1982, pp. 128–138.

Patterson, M. et al., "Acoustics Fields of Conical Radiators," Ultrasonic B–Scan Images, IEEE Transactions on Sonics and Ultrasonics, vol. SU–29, No. 2, Mar. 1982, pp. 83–92.

(List continued on next page.)

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasound transducer that allows transmission of pressure waves at a first frequency and reception of pressure waves at a second frequency. Each transducer element is formed by multiple layers of transducer material. A transceiver provides an excitation signal to the transducer and receives energy from the transducer. All of the layers are coupled to the transceiver during transmission so that all of the layers are activated. Some of the layers are decoupled from the transceiver during reception so that not all of the layers contribute to the received signal.

67 Claims, 9 Drawing Sheets

OTHER PUBLICATIONS

Xu, Q.C. et al., "Composite Transducer with Multiple Piezoelectric Matching Layers," Ultrasonics Symposium, 1988, pp. 507–512.

Bao, X.Q. et al., "Model of a Bilaminar Actuator for Active Acoustic Control Systems," J. Acoust. Soc. Am. 87(3), Mar. 1990, pp. 1350–1352.

Translation of European Patent No. 0 357 164, by J. Atkinson, 1991.

Chofflet, L. et al., "A Multi–Piezoelectric Structure: The Stacked Transducer," Ultrasonics Symposium, 1991 pp. 611–614.

Hossack, J.A. et al., "Multiple Layer Transducers for Broadband Applications," Ultrasonics Symposium, 1991, pp. 605–610.

Schrope, B. et al., "Simulated Capillary Blood Flow Measurement Using a Nonlinear Ultrasonic Contrast Agent," Ultrasonic Imaging 14, 1992, pp. 134–158.

Hossack, J.A. et al., "Improving Transducer Performance Using Multiple Active Layers," SPIE vol. 1733, 1992, pp. 284–296.

Hossack, J.A. et al., "Improving the Characteristics of a Transducer Using Multiple Piezoelectric Layers," IEEE Transactions on Ultrasonics, Ferroelectrics, and Frequency Control, vol. 40, No. 2, Mar. 1993, pp. 131–139.

Russell, L.B. et al., "Thickness–Mode Modeling of Active Multi–Layered Piezoelectric Transducers and the Application to "SMART" Sensor Design," Ultrasonics Symposium, 1994, pp. 615–618.

Strout, T., et al., "Relaxor Ferroelectric Materials," Ultrasonics Symposium, 1990, pp. 711–720.

Takeuchi, H., et al., "Medical Ultrasonic Probe Using Electrostrictive–Ceramics/Polymer Composite," Ultrasonics Symposium, 1989, pp. 705–708.

D. Damjanovic, et al., "Electrostrictive and Piezoelectric Materials for Actuator Applications," J. of Intell. Mater. Syst. and Struct., vol. 3, Apr. 1992, pp. 190–208.

TRANSDUCER RESPONSE (—) AND DESIRED TRANSMIT AND RECEIVE RESPONSES (-)

DESIRED (-) AND OBTAINED RESULTS (—)

EXTENDED BANDWIDTH ULTRASONIC TRANSDUCER

This application is a continuation of U.S. application Ser. No. 08/661,227, filed Jun. 10, 1996.

FIELD OF THE INVENTION

This invention relates to transducers and more particularly to phased array transducers for use particularly in the medical diagnostic field.

Ultrasound machines are often used for observing organs in the human body. Typically, these machines contain transducer arrays for converting electrical signals into pressure waves and vice versa. Generally, the transducer array is in the form of a hand-held probe which may be adjusted in position to direct the ultrasound beam to the region of interest.

FIG. 1 illustrates a prior art transducer array 10 for generating an ultrasound beam. Typically, such an array may have 128 transducer elements 12 in the azimuthal direction. Adapted from radar terminology, the x, y, and z directions are referred to as the azimuthal, elevation, and range directions, respectively.

Each transducer element 12, typically rectangular in cross-section, includes a first electrode 14, a second electrode 16 and a piezoelectric layer 18. In addition, one or more acoustic matching layers 20 may be disposed over the piezoelectric layer 18 to increase the efficiency of the sound energy transfer to the external medium. The electrode 14 for a given transducer element 12 may be part of a flexible circuit 15 for providing the hot wire or excitation signal to the piezoelectric layer 18. Electrode 16 for a given transducer element may be connected to a ground shield return 17. The piezoelectric layer 18 is metalized on its top and bottom surfaces and the matching layer 20 is also metalized on all surfaces so that electrode 16 which is in physical contact with the matching layer 20 is electrically coupled to a surface of the piezoelectric layer 18 by the metallization.

The transducer elements 12 are disposed on a backing block 24. The backing block 24 may be highly attenuative such that ultrasound energy radiated in its direction (i.e., away from an object 32 of interest) is substantially absorbed. In addition, a mechanical lens 26 may be placed on the matching layer 20 to help confine the generated beam in the elevation-range plane and focus the ultrasound energy to a clinically useful depth in the body. The transducer array 10 may be placed in a nose piece 34 which houses the array. Examples of prior art transducer structures are disclosed in Charles S. DeSilets, *Transducer Arrays Suitable for Acoustic Imaginq*, Ph.D. Thesis, Stanford University (1978) and Alan R. Selfridge, *Design and Fabrication of Ultrasonic Transducers and Transducer Arrays*, Ph.D. Thesis, Stanford University (1982).

Individual elements 12 are electrically excited by electrodes 14 and 16 with different amplitude and phase characteristics to steer and focus the ultrasound beam in the azimuthal-range plane. An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce a focused image on the display screen. When an electrical signal is imposed across the piezoelectric layer 18, the thickness of the layer changes slightly. This property is used to generate sound from electrical energy. Conversely, electrical signals are generated across the electrodes in contact with the piezoelectric layer 18 in response to thickness changes that have been imposed mechanically from sound waves reflected back to the piezoelectric layer 18.

The pressure waves generated by the transducer elements 12 are directed toward an object 32 to be observed, such as the heart of a patient being examined. Each time the pressure wave confronts tissue having different acoustic characteristics, a wave is reflected backward. The array of transducers may then convert the reflected pressure waves into corresponding electrical signals.

For the transducer shown in FIG. 1 the beam is said to be mechanically focused in the elevation direction. The focusing of the beam in the azimuthal direction is done electronically by controlling the timing of the transmissions of each transducer element. This may be accomplished by introducing appropriate phase delays in the firing signals.

Reflected energy from a particular location in the imaging plane is collected by the transducer elements. The resultant electronic signals from individual transducer elements are individually detected and reinforced by introducing appropriate delays. Extensive processing of such data from the entire imaging phase is done to generate an image of the object. Such an image is typically displayed on a CRT monitor.

Sometimes it is desirable to image particular features to the exclusion of others. For example, it may be desirable to image the flow of blood in a patient to the exclusion of the surrounding organs and muscles. Introducing contrast agents into the patient's bloodstream allows the imaging of the blood stream. Contrast agents may be in the form of a solution or suspension of microbubbles or agents that produce microbubbles. The use of contrast agents provides selective evaluation of the signal components affected by the materials or media which have been introduced. This has the advantage that selective representation of the region filled with those agents is possible without finding the difference between two or more conditions recorded before and after application of the materials or media.

Nonlinear contrast agents are described for example by V. Uhlendorf, et al., in "Nonlinear Acoustical Response of Coated Microbubbles in Diagnostic Ultrasound" (1995) Ultrasonic Symposium, pp. 1559–1562). Such agents possess a fundamental resonant frequency. When they are insonified with high intensity ultrasonic energy at this fundamental frequency, they radiate ultrasonic frequency at a harmonic of the fundamental frequency. Such contrast agents are often used to highlight regions containing blood loaded with the contrast agent. For example, in the case of a blood-filled chamber of the heart, the borders of the chamber can be distinguished more easily when contrast agent is used. Since the contrast agent generates harmonic ultrasound energy, echoes from tissue (containing no contrast agent) at the fundamental frequency may be eliminated by filtering at the receive beamformer. Because most transducers operate in the half wavelength resonance mode they are not able to effectively receive energy at a second harmonic frequency since at the second harmonic frequency, the transducer elements are approximately one wavelength thick. This causes the charge generated on the two halves of the transducer element to be out of phase with each other which results in a cancellation or a null.

A wideband transducer can be operated to transmit pressure waves at one frequency and receive second harmonic frequency signals reflected back. FIG. 2 is a graph illustrating the transmit response from a transducer having a wide bandwidth, for example 70%. A bandwidth of 70% means that the bandwidth measured between the lower frequency at which the sensitivity is −6 dB with respect to the maximum sensitivity attained over the useful frequency range of the transducer and the upper frequency at which the sensitivity is −6 dB with respect to the maximum sensitivity is 70% of the center frequency where the center frequency is defined as the average of the lower and upper −6 dB frequencies. Using a transducer with a center frequency $f_c$ of 4.5 MHz, an ultrasound wave can be transmitted at ⅔ $f_c$ or 3 MHz and received at 4/3 $f_c$ or 6 MHz.

While energy may be transmitted and received within the transducer's available bandwidth, there are several disadvantages associated with using a wideband transducer in such a manner. Because transducer bandwidths are typically 75% and less, it is necessary to work near the edges of the transducer's bandwidth in order to transmit at one frequency and receive at another. This results in lower sensitivity and undesirable filtering effects on the lower edge of the spectrum in transmit and on the upper end of the spectrum on receive as will be illustrated in the graphs of FIGS. 3 and 4. Ideally it is desirable to operate near the center of the available bandwidth for maximum sensitivity and spectral purity.

FIG. 3 is a graph illustrating the transducer transmit response (in dashed line) and the desired transmit response and receive response centered at ⅔ $f_c$ and 4/3 $f_c$ respectively (in solid line). FIG. 4 is a graph illustrating the filtering effect of operating a wide bandwidth transducer near the edges of its bandwidth. The desired transmit and receive response are shown in solid line and the distorted, filtered transmit and receive response are shown in dashed line. It can be seen that a portion of the desired spectra has been removed by the filtering effect of the transducer.

It is thus desirable to provide a transducer structure that can be optimized to transmit pressure waves at one frequency and receive energy at another frequency. More particularly, it is desirable to provide a transducer that can generate pressure waves at a first fundamental frequency and receive pressure waves at a second harmonic frequency.

SUMMARY OF THE INVENTION

According to a first aspect of the present invention there is provided an ultrasound transducer probe for transmitting an ultrasound beam into an area of examination and receiving signals reflected from said area of examination. The ultrasound transducer probe includes a first layer having a first electrode on one side of the first layer and a second electrode on an opposite side of the first layer. The first layer emits an ultrasound beam when a signal is applied to the first and second electrodes and the first layer develops a signal across the first and second electrodes upon receipt of an ultrasound beam reflected back from the area of examination. A second layer is disposed on the first layer. The second layer has a third electrode on one side of the second layer and a fourth electrode on an opposite side of the second layer. The second layer emits an ultrasound beam when a signal is applied to the third and fourth electrodes and the second layer develops a signal across the third and fourth electrodes upon receipt of an ultrasound beam reflected back from the area of examination. Means for isolating the signal developed across the second layer are provided.

According to a second aspect of the present invention there is provided a method for imaging an area of examination by transmitting an ultrasound beam into the area of examination and receiving signals reflected back from the area of examination. The method includes the steps of providing an ultrasound transducer having at least a first layer and a second layer, disposed on the first layer, transmitting an ultrasound beam by applying a signal across both the first and second layers, and receiving signals generated across the first layer while isolating signals generated across the second layer.

According to a third aspect of the present invention there is provided a method for imaging an object by projecting an ultrasound beam onto the object to be imaged and analyzing signals reflected from the object, the method includes the steps of providing an ultrasound transducer having a first layer of piezo-electrically active material and a second layer of piezoelectrically active material disposed on the first layer, operating the transducer in a transmit mode by activating the first and second layers, switching the transducer from the transmit mode to a receive mode wherein signals generated in the second layer are isolated from signals developed in the first layer and only signals developed in the first layer are analyzed.

According to a fourth aspect of the present invention there is provided a method for imaging an area of examination by transmitting an ultrasound beam into the area of examination and receiving signals reflected back from the area of examination. The method includes the steps of providing an ultrasonic transducer having a plurality of transducer segments, each transducer segment formed by at least a first layer of piezoelectric material and a second layer of piezoelectric material disposed on the first layer of piezoelectric material, activating both the first and said second layers to transmit an ultrasound beam, and isolating signals developed across the second layer during reception of an ultrasound beam reflected back from the area of examination.

According to a fifth aspect of the present invention there is provided a method for imaging an area of examination. The method includes the steps of providing an ultrasound transducer having a plurality of transducer segments, each transducer segment having at least a first layer of piezoelectric material and a second layer of piezoelectric material disposed on the first layer, operating the ultrasound transducer in a transmit mode whereby both the first and the second layer are activated thereby causing an ultrasound beam to be transmitted into the area of examination by the ultrasound transducer, switching the ultrasound transducer from the transmit mode to a receive mode whereby an ultrasound beam reflected back from the area of examination develops a signal across the first and second layers, isolating the signal developed across the second layer, and analyzing the signal developed across the first layer.

According to a sixth aspect of the present invention there is provided an ultrasound system for generating an image of an object located in an area of examination. The system includes a transducer probe for transmitting an ultrasound signal at a first frequency and receiving an ultrasound signal at a second harmonic frequency, transmit circuitry for transmitting signals to a transducer probe and receive circuitry for processing the signals received by the transducer probe. The transducer probe includes transducer elements where each transducer element is formed by a first layer of piezoelectric material and a second layer of piezoelectric material disposed on said first layer wherein the transmit circuitry is electrically coupled to both the first and second layers and the receive circuitry is electrically coupled to the first layer but electrically decoupled from the second layer.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 1:
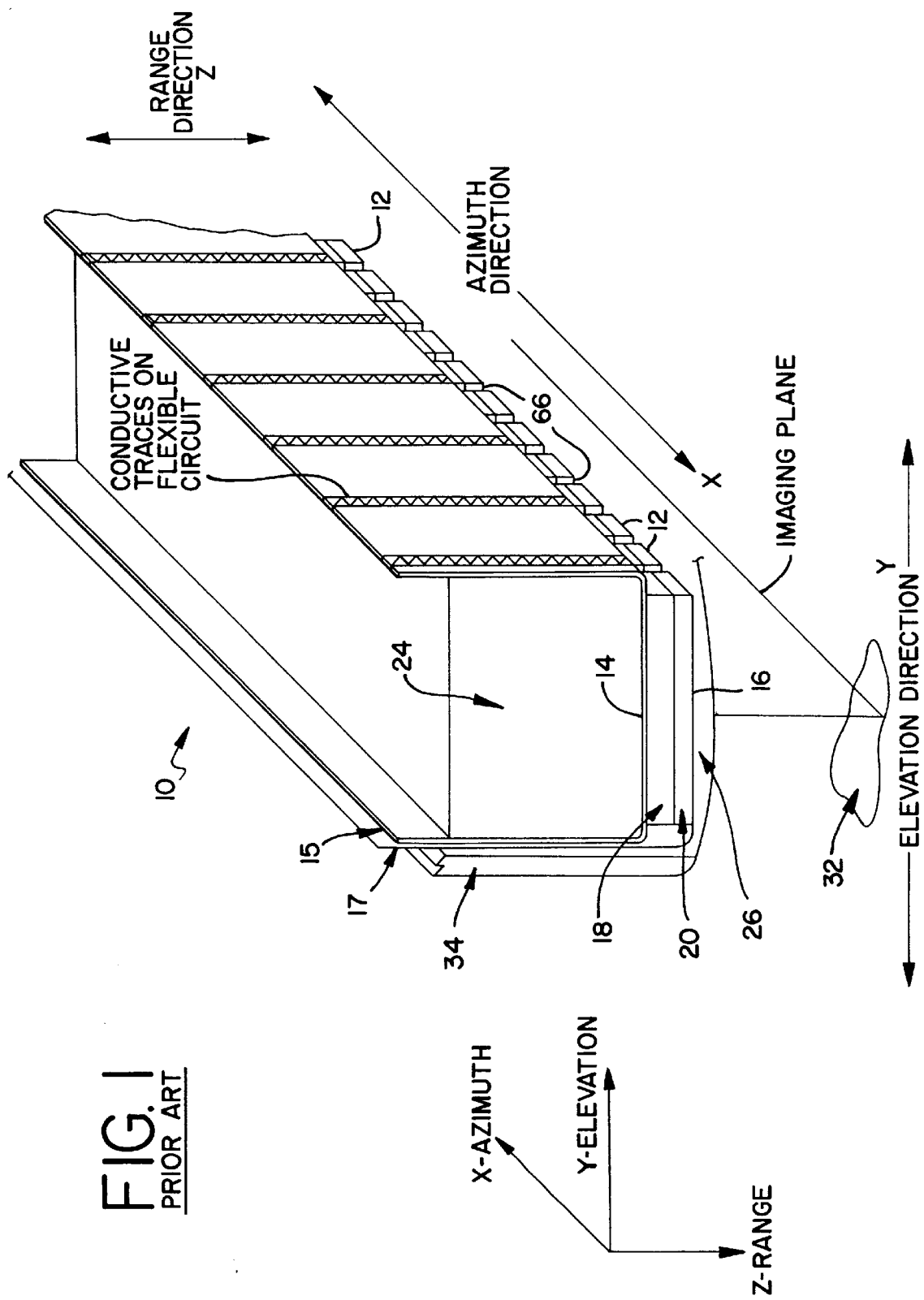
FIG. 1 illustrates a prior art transducer array for generating an ultrasound beam.
Figure 2:
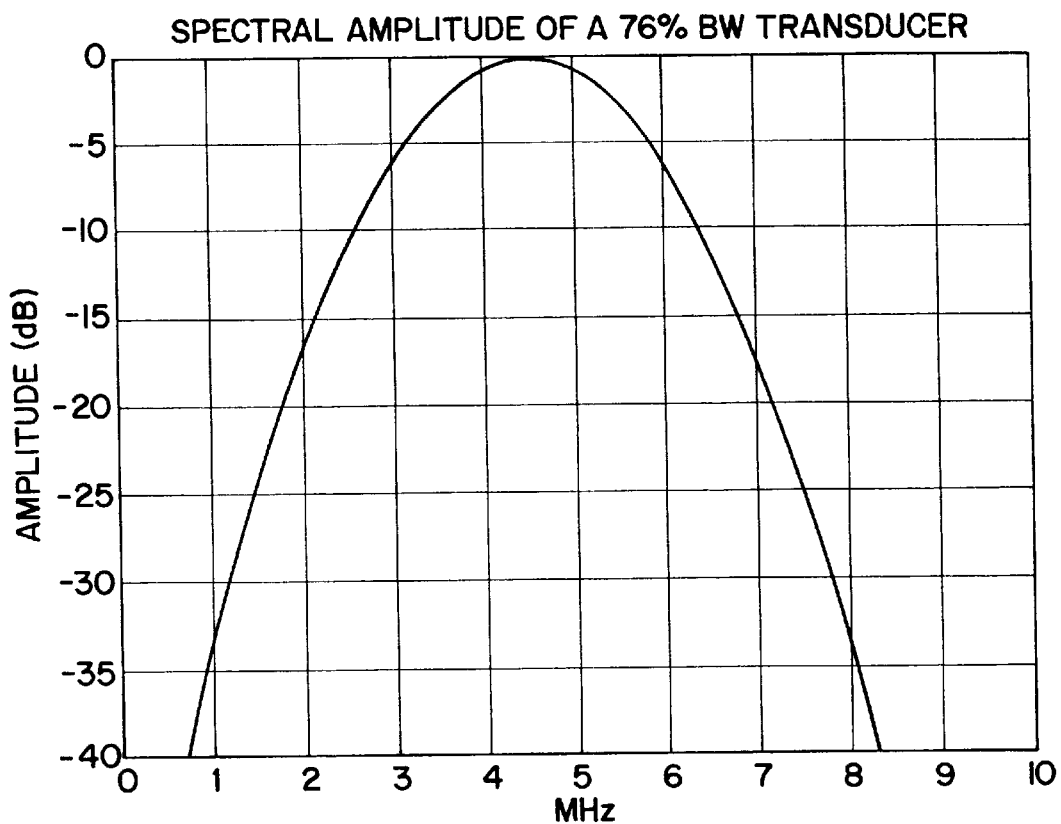
FIG. 2 is a graph illustrating the transmit response from a transducer having a wide bandwidth.
Figure 5:
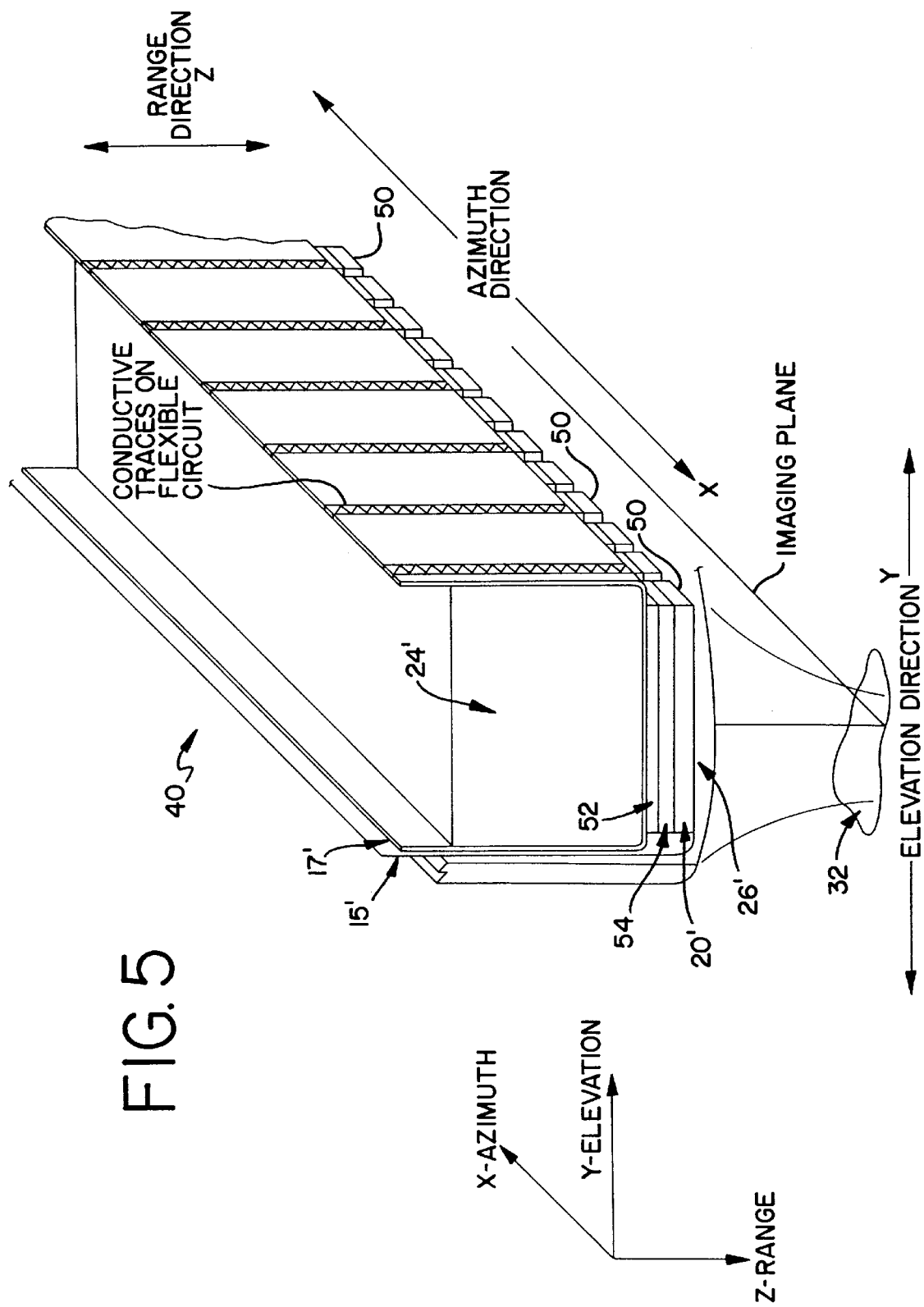
FIG. 5 is a schematic view of a transducer array according to a first preferred embodiment of the present invention.

FIG. 5 is a schematic of a transducer array 40 according to a first preferred embodiment of the present invention. The transducer array 40 has many of the same components as the transducer array 10 shown in FIG. 1. Therefore, like reference numerals, primed, will be used to identify like components. The transducer array 40 includes a backing block 24', an interconnecting or flexible circuits 15' and 17' and a plurality of transducer elements 50. In a preferred embodiment, the transducer array 40 includes one or more acoustic matching layers 20' disposed over the transducer elements 50. In addition, a lens 26' may be placed on the acoustic matching layer 20'. The plurality of transducer elements 50 are arranged along the azimuthal direction.

Each transducer element 50 is formed by multiple layers of transducer material. In a preferred embodiment a double layer transducer is shown having a first layer 52 and a second layer 54 disposed on the first layer 52. Of course, more than two layers may be provided. In addition, an intermediate layer or layers, piezoelectric or non piezoelectric, may be disposed between the first and second layers. Multilayer transducers are typically employed where it is necessary to stack transducer layers in order to improve electrical matching to cable and system. Such stacked layers are acoustically in series and electrically in parallel. The flexible circuits 15' and 17' are coupled to the electrodes on the first and second layers 52 and 54 of the transducer as will be discussed in detail hereinafter. A third flexible circuit (not shown) is coupled to the abutting electrodes of the first and second layer.

In a preferred embodiment, the first and second layers 52 and 54 are composed of lead zirconate titanate (PZT) such as 3203HD commercially available from Motorola Ceramic Products of Albuquerque, N.Mex. Alternatively, the first and second layers 52 and 54 may be formed from a composite material of piezoelectric ceramic posts embedded in polymer or PVDF piezoelectric polymer material. In addition, both layers do not have to be made of the same material. One could be formed from PZT while the other is a PZT composite or PVDF layer, for example. The first layer 52 and the second layer 54 each preferably have a thickness of about 0.009 inches. Alternatively, the thickness of each layer may range from about 0.006 to about 0.012 inches. In addition, both layers need not have the same thickness.

In a preferred embodiment the backing block 24' is formed of a filled epoxy comprising Dow Corning's part number DER 332 treated with Dow Corning's curing agent DEH 24 and has an aluminum oxide filler. Preferably the acoustic matching layer 20 or layers may have a high impedance or a low impedance or both when multiple matching layers are used. A low impedance matching layer may be formed of Dow Corning's epoxy DER 332 plus Dow Corning's curing agent DEH 24. For a high impedance acoustic matching layer the same materials may be used plus a filler of 1 micron tungsten carbide and 9 micron alumina particles which are added to obtain an acoustic impedance of approximately 10.0 MRayls.

Figure 6:
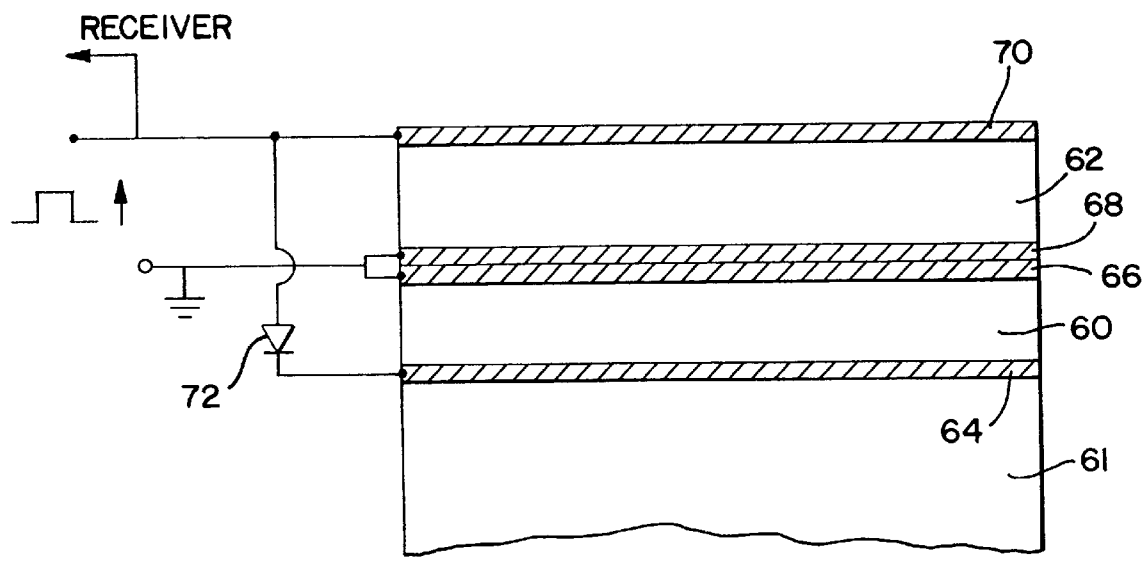
FIG. 6 illustrates a cross-sectional view taken along the elevation direction of a transducer array according to a preferred embodiment of the present invention.
Figure 3:
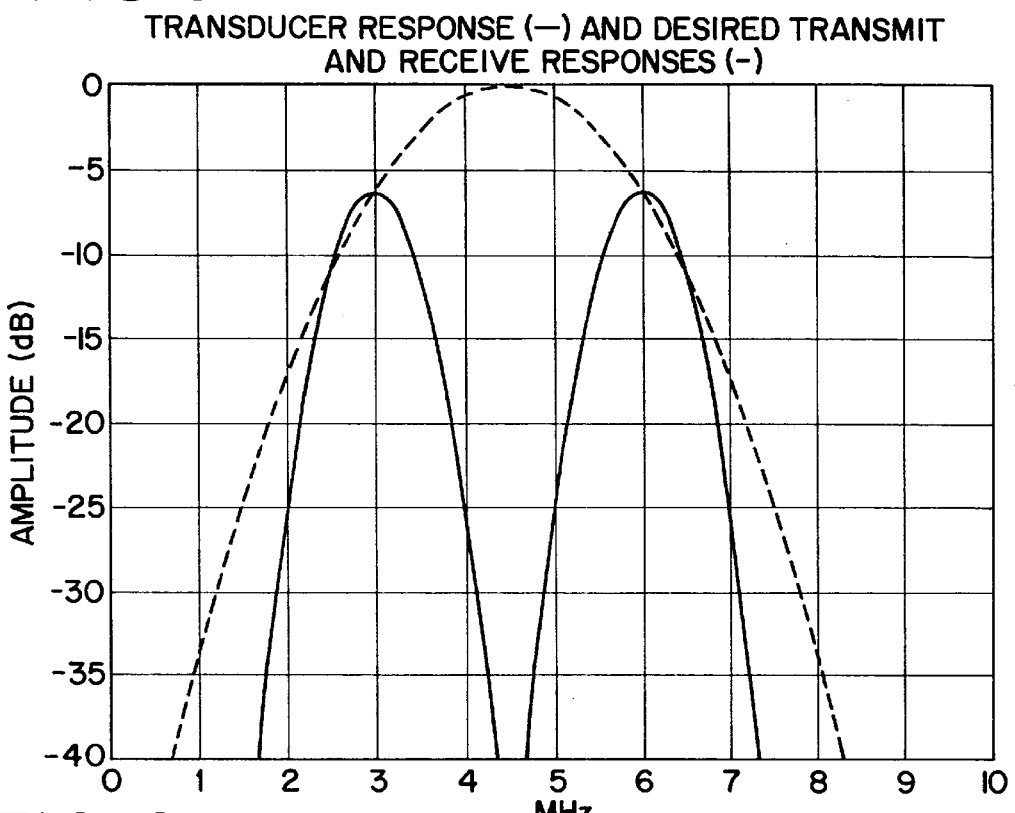
FIG. 3 is a graph illustrating the transducer transmit response and the desired transmit response and receive response.
Figure 4:
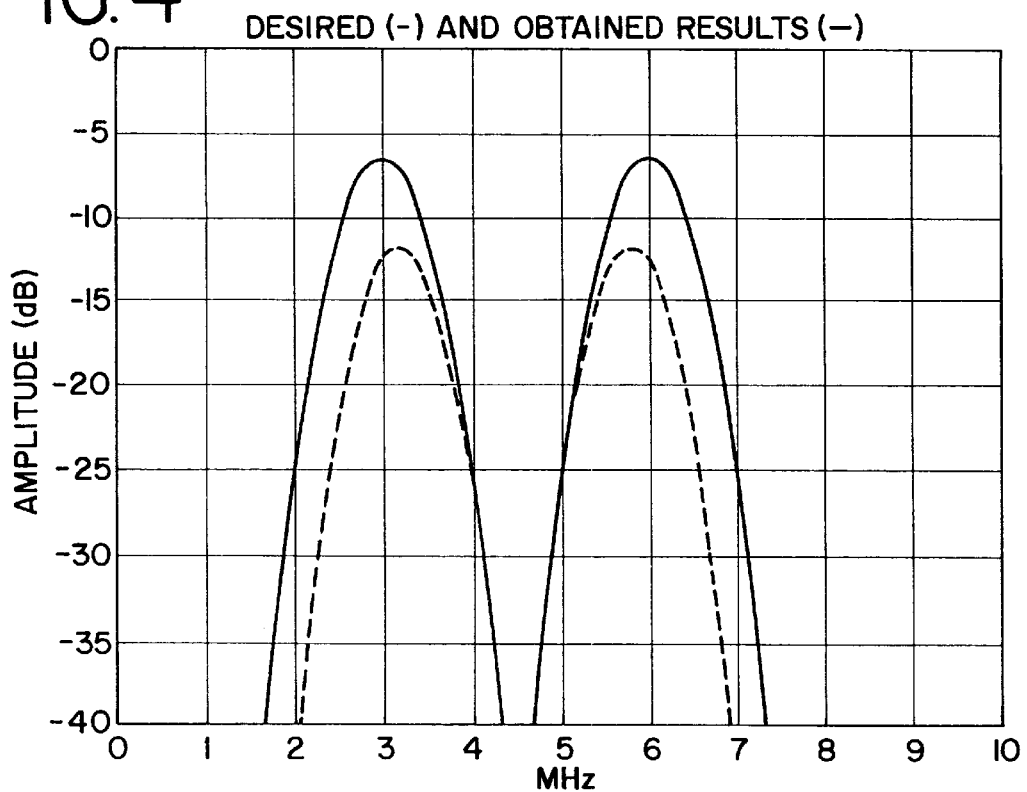
FIG. 4 is a graph illustrating the filtering effect of operating a wide bandwidth transducer near the edges of its bandwidth.

FIG. 6 illustrates a cross-sectional view taken along the elevation direction of a transducer array according to a preferred embodiment of the present invention. The transducer array preferably includes a first layer 60 of piezoelectric material and a second layer 62 of piezoelectric material disposed on the first layer 60. Both layers are disposed on a backing block 61. The first layer 60 has a first electrode 64 on one surface and a second electrode 66 on an opposite surface. The second layer 62 also has a first electrode 68 on one surface and a second electrode 70 on an opposite surface. Alternatively, electrodes 66 and 68 may be formed as one electrode between the first and second layer. Standard electrodes are available from the PZT manufacturer. Preferably the electrodes are formed of gold sputtered over a nickel chrome adhesion layer.

The second electrode 66 of the first layer 60 and the first electrode 68 of the second layer 62 abut one another and are coupled to ground as shown. The second electrode 70 of the second layer 62 is preferably permanently coupled to a transceiver (not shown) of the transducer system. The first electrode 64 of the first layer 60 is coupled to the transceiver through a diode 72.

The first electrode 64 of the first layer 60 and the second electrode 70 of the second layer 62 may be part of a flexible circuit such as 15' and 17' as shown in FIG. 5 for providing the hot wire or excitation signal to the first and second layers 60 and 62, respectively. A flexible circuit may be any interconnecting design used in the acoustic or integrated circuit fields, for example. The flexible circuit is typically made of a copper layer carrying a lead for exciting the transducer element. The copper layer may be bonded to a piece of polyimide material, typically KAPTON. In the region of the transducer element both sides of the copper flexible circuit should be exposed, i.e. free from polyimide so that electrical contact to the top and bottom electrodes of the piezoelectric layers is facilitated. Preferably the copper layer is coextensive in size with the transducer element. In addition, the interconnect circuit may be gold plated to improve the contact performance. Such a flexible circuit is manufactured by Sheldahl of Northfield, Minn. The ground electrode may also be formed by a flexible circuit.

The transceiver transmits an excitation signal to the transducer array and receives signals from the transducer array. In this particular embodiment the transceiver emits an excitation signal in the form of a positive pulse as shown. The voltage of the excitation signal is generally significantly greater than the diode turn-on voltage and thus during transmit, both the first and second layers 60 and 62 are activated. The excitation signal may be modified to accommodate the presence of diode 72 so that the voltage across the first layer 60 is as required, i.e., if the diode has a voltage drop of 0.7 volts, the amplitude of the excitation signal may be increased by 0.7 volts.

In the reception mode, the voltage generated across the first layer 60 and the second layer 62 from a pressure wave reflected back by the object being examined is on the order of a few millivolts. The voltage across the first layer 60 does not exceed the turn-on voltage of the diode 72. Therefore diode 72 isolates the first layer 60 from the transceiver during reception. Alternatively, the second layer 62 may be isolated by coupling a diode in series with the signal connection to the second layer 62. In addition, more than one diode may be used depending upon the magnitude of the voltage generated across a layer. The system switches from transmit to receive mode immediately after completion of a transmit pulse.

Figure 7:
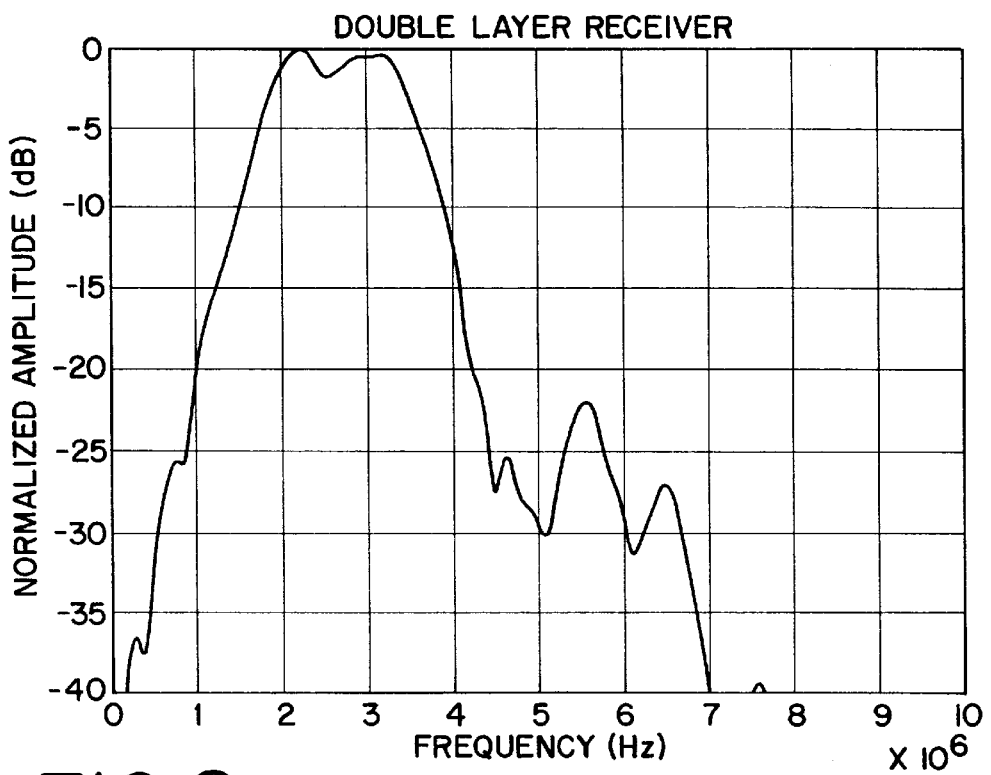
FIG. 7 is a graph illustrating the receive response of a double layer transducer in which both layers are connected in parallel.

FIG. 7 is a graph illustrating the receive response of a double layer transducer in which both layers are electrically connected in parallel as they are in transmission. In this embodiment each piezoelectric layer was about 0.25 mm thick, about 14 mm long and about 0.265 mm wide. A high impedance acoustic matching layer having a thickness of about 0.126 mm and a low impedance matching layer having a thickness of 0.087 mm were used. The center frequency of the excitation signal was about 2.8 MHz and at the second harmonic, 5.6 MHz, the response was considerably attenuated as shown.

Figure 8:
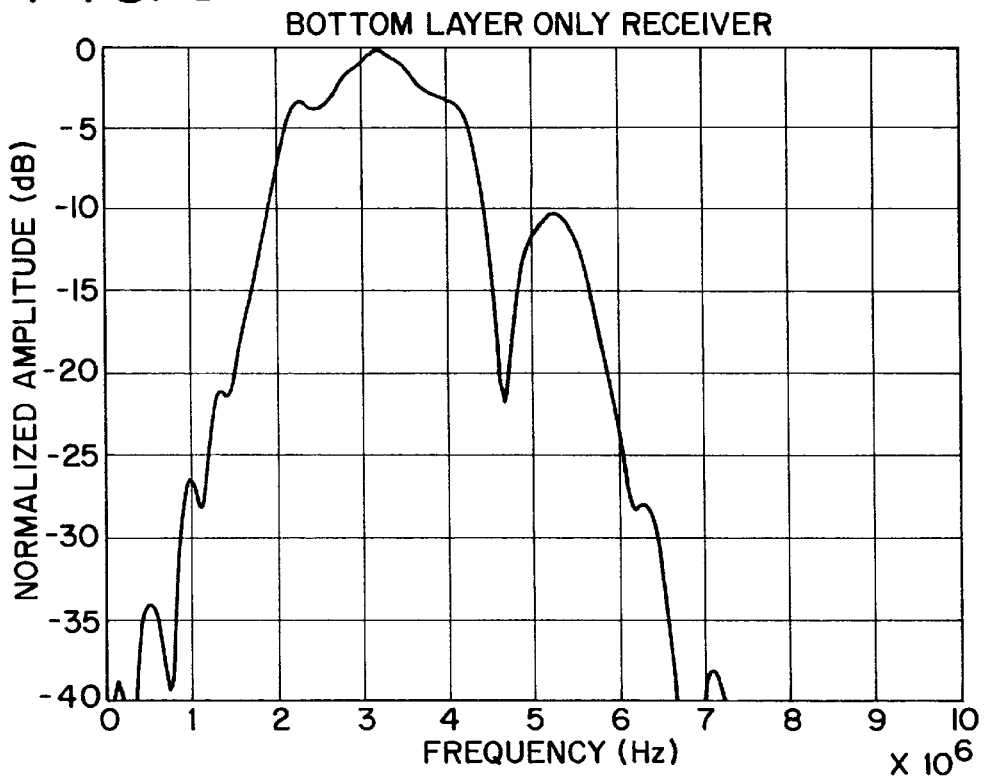
FIG. 8 is a graph illustrating the receive response of the same transducer of FIG. 7 with only the bottom layer connected.

FIG. 8 is a graph illustrating the receive response of the same transducer as that used for FIG. 7 with only the bottom layer coupled to the transceiver during reception while the top layer is isolated. It can be seen from the graph that a significant increase in sensitivity in the vicinity of the second harmonic is produced.

Figure 9:
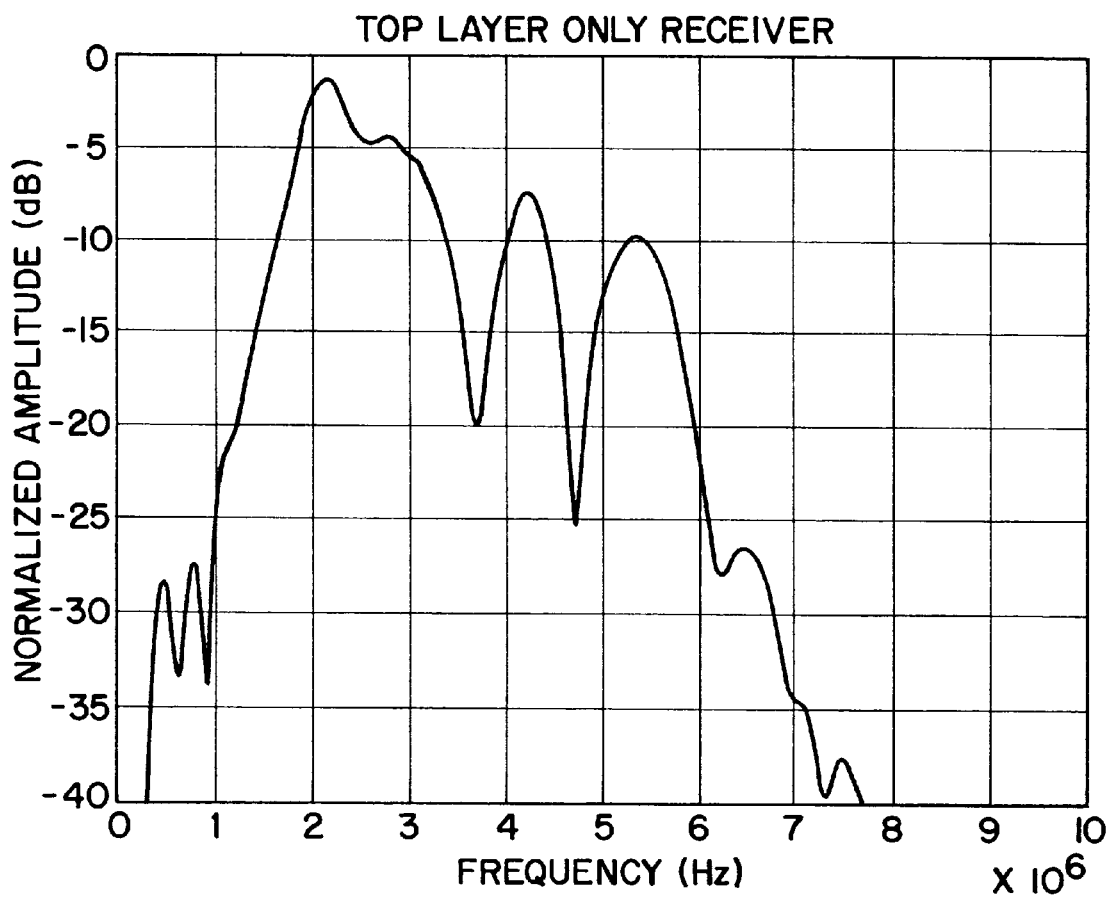
FIG. 9 is a graph illustrating the receive response of the same transducer of FIG. 7 with only the top layer connected.

FIG. 9 is a graph illustrating the receive response of the same transducer as that used for FIG. 7 with only the top layer coupled to the transceiver during reception while the bottom layer is isolated. Again, it can be seen that a significant improvement in sensitivity in the region of the second harmonic has occurred.

Experimentation can be used to optimize the performance of the transducer array varying the dimensions and materials employed.

Of course there are many alternative ways of isolating one or multiple layers of a multi-layer transducer during reception. FIGS. 10–15 illustrate several different preferred embodiments.

Figure 10:
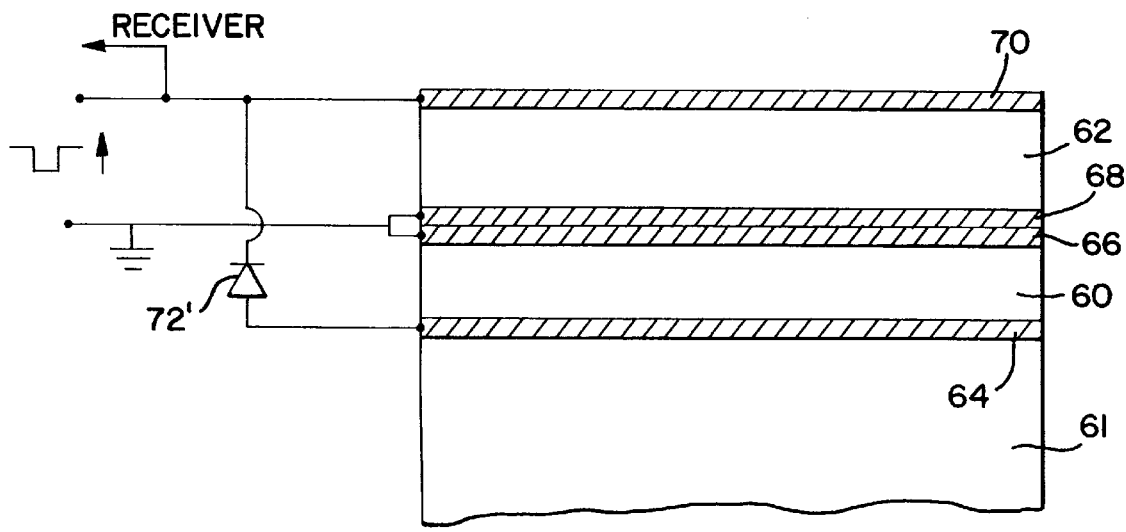
FIG. 10 illustrates a cross-sectional view taken along the elevation direction of a transducer array according to another preferred embodiment of the present invention.

FIG. 10 illustrates a cross-sectional view taken along the elevation direction of a transducer array according to another preferred embodiment of the present invention. The transducer shown in FIG. 10 is similar to that shown in FIG. 6 except that the excitation signal is now a negative pulse and therefore diode 72' is oriented in the opposite sense from that shown in FIG. 6. Otherwise the operation of the transducer is the same and need not be described again.

Figure 11:
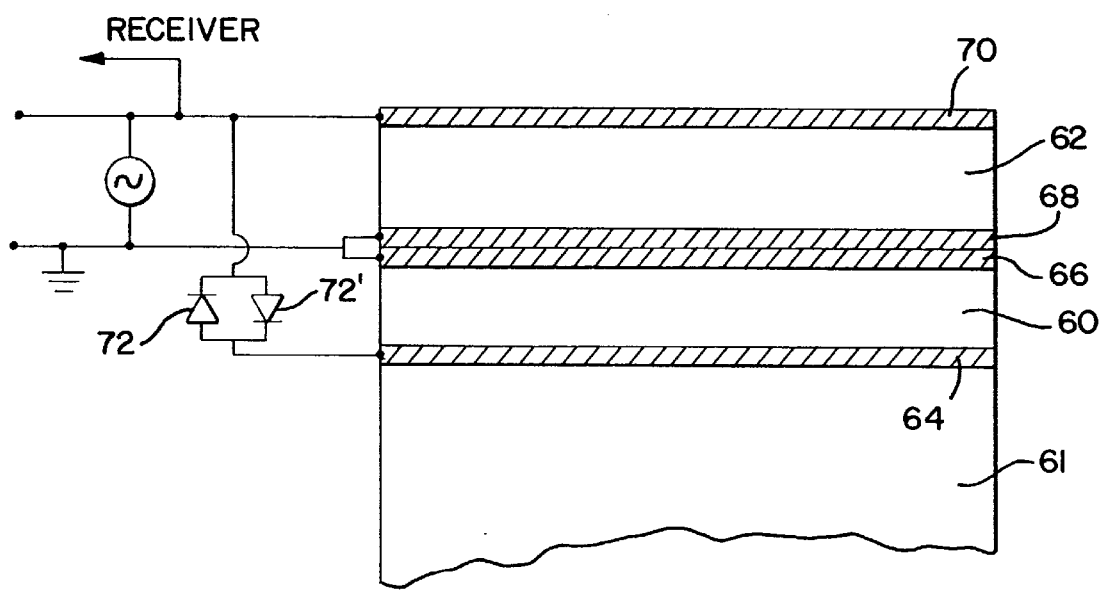
FIG. 11 illustrates a cross-sectional view taken along the elevation direction of a transducer array according to another preferred embodiment of the present invention.

FIG. 11 illustrates a cross-sectional view taken along the elevation direction of a transducer array according to another preferred embodiment of the present invention. In this embodiment the excitation signal is bipolar. Therefore, two diodes 72 and 72' coupled in parallel but in opposite orientations, are coupled in series with the first electrode 64 of the first layer 60 and the transceiver. Again, the diodes 72 and 72' allow the first layer 60 to be active during transmission while isolating the first layer 60 from the transceiver in the receive mode.

Figure 12:
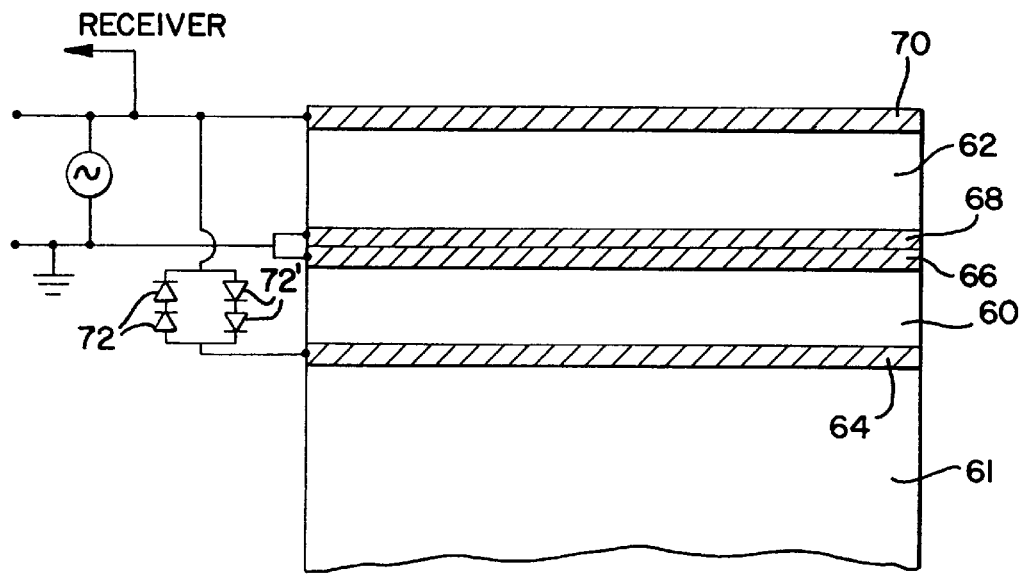
FIG. 12 illustrates a cross-sectional view taken along the elevation direction of a transducer array according to another preferred embodiment of the present invention.
Figure 15:
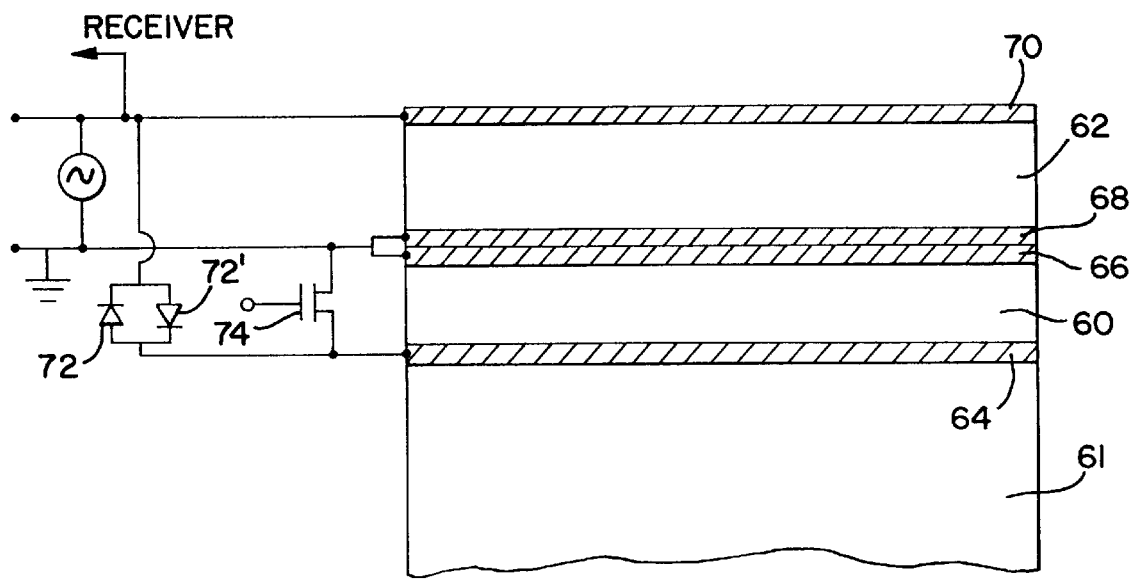
FIG. 15 illustrates a cross-sectional view taken along an elevation direction of a transducer array according to a preferred embodiment of the present invention.

FIG. 12 illustrates a cross-sectional view taken along the elevation direction of a transducer array according to a preferred embodiment of the present invention. The transducer shown in FIG. 15 is similar to that shown in FIG. 11 except that multiple diodes are used in each branch of the arrangement. Providing additional diodes ensures isolation between the first layer 60 and the transceiver should voltages larger than the diode turn-on voltage of one diode be developed across the first layer 60.

Figure 13:
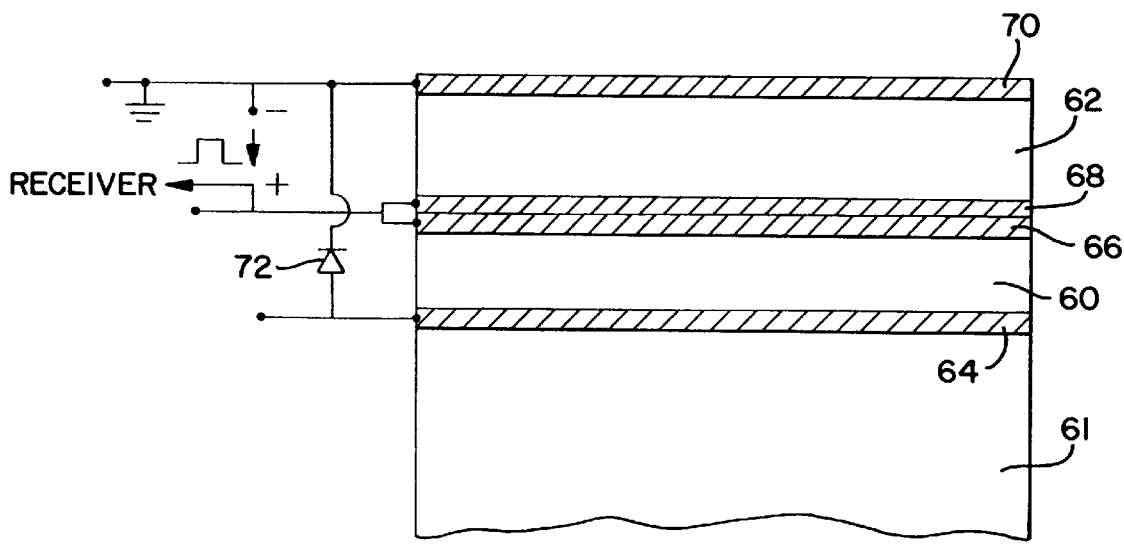
FIG. 13 illustrates a cross-sectional view taken along the elevation direction of a transducer array according to another preferred embodiment of the present invention.

FIG. 13 illustrates a cross-sectional view taken along the elevation direction of a transducer array according to a preferred embodiment of the present invention. In this embodiment the first electrode 64 of the first layer 60 is coupled to ground through diode 72. The second electrode 70 of the second layer 62 is coupled directly to ground. The second electrode 66 of the first layer 60 and the first electrode 68 of the second layer 62 are coupled to the transceiver. This configuration has the advantage that a ground potential electrode is placed closer to the patient and hence a safety improvement is obtained.

Figure 14:
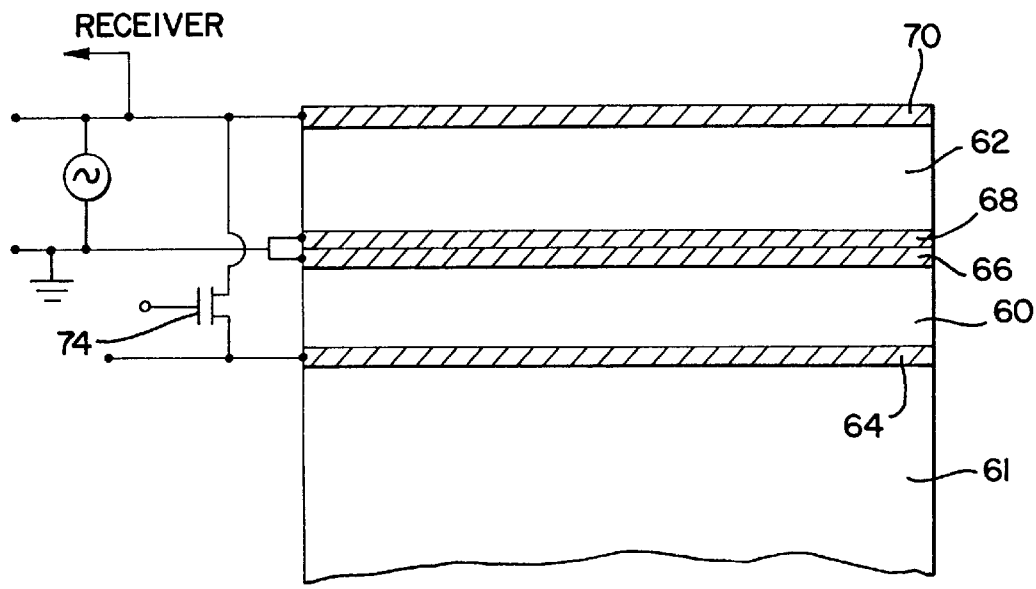
FIG. 14 illustrates a cross-sectional view taken along the elevation direction of a transducer array according to another preferred embodiment of the present invention.

FIG. 14 illustrates a cross-sectional view taken along the elevation direction of a transducer array according to a preferred embodiment of the present invention. The array shown in FIG. 14 is similar to that shown in FIG. 11 except that the diode has been replaced by a transistor 74. The transistor 74 is controlled by an externally applied bias signal which is supplied during transmit to turn on the transistor 74. This effectively connects the hot wire supply to electrode 70 to the wire leading to electrode 64 resulting in dual layer operation in transmit. During receives the transistor 74 is switched off isolating the received voltage generated from layer 60 from that generated across layer 62.

FIG. 15 illustrates a cross-sectional view taken along the elevation direction of a transducer array according to a preferred embodiment of the present invention. In this arrangement, a bipolar excitation signal may be applied to both layers in transmit. In the reception mode, one layer is short circuited by transistor 74. This eliminates the contribution of the second layer to the net received signal. Creating a short circuit across the second layer may have the advantage of reducing cross-talk noise from the second layer interfering with the first layer or adjacent layers in proximal transducer elements. In order to prevent short circuiting the desired signal layer back to back diodes 72 and 72' are provided to isolate the short circuited layer in the event that the receive voltages do not exceed the diode turn-on voltage. Generally the receive signal will not exceed this voltage.

Various modifications may be made to the preferred embodiments illustrated. As shown, the diodes used to isolate the first layer may be replaced by a transistor controlled by an externally applied bias signal. One bias signal can be used for the entire array. Alternatively, the diode can be replaced by an electromechanical switch such as a relay. Of course other means of isolation may be used. For examples any semiconductor device whose electrical conductance may be controlled either by external bias signal or by the transmit pulse itself.

In addition, the ultrasound transducer array may be operated so that it switches between receiving on both layers for optimal conventional imaging and only on one layer for optimal contrast agent detection. More particularly, a single layer would be used in receive for a predetermined time interval after a transmission pulse. This is determined by the maximum useful range of single layer receiver system. The second layer would be switched back on to bring back optimal imaging sensitivity at the fundamental frequency. A predetermined weighting factor would be applied to the line data at the same time to suppress a dramatic change in brightness at the range corresponding to the switching time. Second harmonic data at ranges greater than the range/time of switch on would be largely lost but presumably the field of interest for second harmonic energy would be in the nearer portion of the field of view and hence would not present a problem. The two scans could be interleaved and presented on a display screen together. Such an application could be performed using the embodiments shown in FIGS. 14 and 15 where the bias voltage would be applied to the transistor according to whether or not the response of the first layer was to be isolated.

Also, while only two layers have been illustrated, more than two layers can be used. During the receive cycle switching between single and multiple layer operation may be desired.

In addition, the first and second layers do not have to be of uniform thickness. For example, both layers may have the variable thickness disclosed in U.S. Pat. Nos. 5,415,175 and 5,438,998 which are specifically incorporated herein by reference. Also, the present invention may be implemented with a curved ceramic and a low loss polyurethane filler instead of a lens.

The diode or diodes used to isolate a layer or layers should be selected based on their ability to withstand the design voltages and currents. Motorola MMAD 1108, a 16 pin surface mount package, with eight separate diodes, may be suitable for use in a transducer since package size is an issue. If a transistor is used for isolation, preferably a MOSFET such as National Semiconductor's IRF530 may be used. The selection of the transistor should be based on its ability to withstand the expected voltages and currents and preferably has a low "on" resistance and input capacitance.

It is to be understood that the forms of the invention described herewith are to be taken as preferred examples and that various changes in the shape, size and arrangement of parts may be resorted to, without departing from the spirit of the invention or scope of the claims.

What is claimed is:

1. An ultrasound transducer probe for transmitting an ultrasound beam into an area of examination and receiving signals reflected from said area of examination, the ultrasound transducer probe comprising:

a first layer having a first electrode on one side of said first layer and a second electrode on an opposite side of said first layer wherein said first layer emits an ultrasound beam when a transmit signal is applied to said first and second electrodes and said first layer develops a receive signal across said first and second electrodes upon receipt of an ultrasound beam reflected back from said area of examination;

a second layer disposed on said first layer, said second layer having a third electrode on one side of said second layer and a fourth electrode on an opposite side of said second layer wherein said second layer emits an ultrasound beam when a transmit signal is applied to said third and fourth electrodes and said second layer develops a receive signal across said third and fourth electrodes upon receipt of an ultrasound beam reflected back from said area of examination; and means for isolating said receive signal developed across said second layer.

2. An ultrasound transducer according to claim 1 wherein said second electrode and said third electrode comprise one electrode.

3. An ultrasound transducer according to claim 1 wherein said first and second layers comprise piezoelectric material.

4. An ultrasound transducer according to claim 1 wherein said means for isolating comprises a diode.

5. An ultrasound transducer according to claim 1 wherein said means for isolating comprises a transistor controlled by an externally applied bias voltage.

6. An ultrasound transducer according to claim 1 wherein said first layer and said second layer have a non-uniform thickness.

7. An ultrasound transducer according to claim 1 wherein said first layer and said second layer have a uniform thickness.

8. An ultrasound transducer according to claim 1 wherein the first layer and the second layer are of different thickness.

9. An ultrasound transducer according to claim 1 wherein the first layer comprises a different material than the second layer.

10. A method for imaging an area of examination by transmitting an ultrasound beam into said area of examination and receiving signals reflected back from said area of examination, the method comprising the steps of:

providing an ultrasound transducer having at least a first layer and a second layer said second layer disposed on said first layer;

transmitting an ultrasound beam by applying a signal across both said first and second layers; and receiving signals generated across said first layer while isolating signals generated across said second layer.

11. A method according to claim 10 further comprising the steps of switching from receiving signals generated across said first layer while isolating signals generated across said second layer and receiving signals generated across both said first and second layers.

12. A method for imaging according to claim 10 wherein said first and second layers comprise piezoelectrically active material.

13. A method for imaging an object by projecting an ultrasound beam onto said object to be imaged and analyzing signals reflected from said object, the method comprising the steps of:

providing an ultrasound transducer having a first layer of piezoelectrically active material and a second layer of piezoelectrically active material disposed on said first layer;

operating said transducer in a transmit mode by activating said first and second layers;

switching said transducer from said transmit mode to a receive mode wherein signals generated in said second layer are isolated from signals developed in said first layer.

14. A method for imaging an area of examination by transmitting an ultrasound beam into said area of examination and receiving signals reflected back from said areas of examination, the method comprising the steps of:

providing an ultrasonic transducer having a plurality of transducer segments, each transducer segment formed by at least a first layer of piezoelectric material and a second layer of piezoelectric material disposed on said first layer of piezoelectric material;

activating both said first and said second layer to transmit ultrasound beam; and isolating signals developed across said second layer during reception of an ultrasound beam reflected back from said area of examination.

15. A method for imaging an area of examination, the method comprising the steps of:

providing an ultrasound transducer having a plurality of transducer segments, each transducer segment having at least a first layer of piezoelectric material and a second layer of piezoelectric material disposed on said first layer;

operating said ultrasound transducer in a transmit mode whereby both said first and said second layer are activated thereby causing an ultrasound beam to be transmitted into said area of examination by said ultrasound transducer;

switching said ultrasound transducer from said transmit mode to a receive mode whereby an ultrasound beam reflected back from said area of examination develops a signal across said first and said second layers;

isolating said signal developed across said second layer; and analyzing said signal developed across said first layer.

16. An ultrasound system for generating an image of an object located in an area of examination, said system comprising:

a transducer probe for transmitting an ultrasound signal at a first frequency and receiving an ultrasound signal at a second harmonic frequency;

transmit circuitry for transmitting signals to a transducer probe; and receive circuitry for processing the signals received by the transducer probe, wherein said transducer probe includes transducer elements where each transducer element is formed by a first layer of piezoelectric material and a second layer of piezoelectric material disposed on said first layer wherein said transmit circuitry is electrically coupled to both said first and second layers and said receive circuitry is electrically coupled to said first layer but electrically decoupled from said second layer.

17. An ultrasound system according to claim 16 wherein said first and second layers have a uniform thickness.

18. An ultrasound system according to claim 16 wherein said first and second layers have a non-uniform thickness.

19. An ultrasound system according to claim 16 wherein said receive circuitry is electrically decoupled from said second layer by a diode coupled between said receive circuitry and said second layer.

20. An ultrasound system according to claim 16 wherein said receive circuitry is electrically decoupled from said second layer by a transistor coupled between said receive circuitry and said second layer, said system further comprising a source of bias voltage coupled to said transistor to control the switching of said transistor wherein said transistor is turned on during the receive mode and off during the transmit mode or off during the receive mode and on during the transmit mode.

21. A method according to claim 11 wherein the switching step is determined by a maximum useful range of a single layer system.

22. A method according to claim 21 further comprising the step of applying a weighing factor to the received signals to suppress a dramatic change in brightness at the switching time.

23. An ultrasound system according to claim 16 wherein said receive circuitry is electrically decoupled from said second layer by an electromechanical switch coupled between said receive circuitry and said second layer.

24. An ultrasound system according to claim 23 wherein the electromechanical switch is a relay.

25. A method for imaging an area of examination by transmitting an ultrasound beam into said area of examination and receiving signals reflected back from said area of examination, the method comprising the steps of:

providing an ultrasound transducer having a multiple number of layers disposed one on top of the other;

transmitting an ultrasound beam by applying a signal across each one of the multiple number of layers; and receiving signals generated across at least one layer less than the multiple number of layers used to transmit the ultrasound beam.

26. A method according to claim 25 further comprising the steps of switching from receiving signals generated across at least one layer less than the number of multiple layers used to transmit the ultrasound beam and receiving signals generated across all of the multiple number of layers.

27. A method for imaging according to claim 25 wherein said multiple number of layers comprise piezoelectrically active material.

28. A method for imaging an object by projecting an ultrasound beam into said object to be imaged and analyzing signals reflected from said object, the method comprising the steps of:

providing an ultrasound transducer having a multiple number of layers of piezoelectrically active material;

operating said transducer in a transmit mode by activating all of said multiple number of layers;

switching said transducer from said transmit mode to a receive mode wherein signals generated in at least one layer of the multiple number of layers is isolated.

29. An ultrasound system for generating an image of an object located in an area of examination, said system comprising:

a transducer probe for transmitting an ultrasound signal at a first frequency and receiving an ultrasound signal at a second harmonic frequency;

transmit circuitry for transmitting signals to a transducer probe; and receive circuitry for processing the signals received by the transducer probe, wherein said transducer probe includes transducer elements where each transducer element is formed by a multiple number of layers of piezoelectric material disposed on each other wherein said transmit circuitry is electrically coupled to the multiple number of layers and said receive circuitry is electrically coupled to at least one layer less than the multiple number of layers.

30. An ultrasound system according to claim 29 wherein said multiple number of layers have a uniform thickness.

31. An ultrasound system according to claim 29 wherein said multiple number of layers have a non-uniform thickness.

32. An ultrasound system according to claim 29 wherein said receive circuitry is electrically decoupled from the at least one layer less than the multiple number of layers by a diode coupled between said receive circuitry and the at least one layer less than the multiple number of layers.

33. An ultrasound system according to claim 29 wherein said receive circuitry is electrically decoupled from the at least one layer less than the multiple number of layers by a transistor coupled between said receive circuitry and the at least one layer less than the multiple number of layers, said system further comprising a source of bias voltage coupled to said transistor to control the switching of said transistor wherein said transistor is turned on during the receive mode and off during the transmit mode or off during the receive mode and on during the transmit mode.

34. A method according to claim 11 wherein the step of isolating signals generated across said second layer comprises providing an open circuit between said second layer and a receiver.

35. A method according to claim 11 wherein the step of isolating signals generated across said second layer comprises providing a short circuit across said second layer.

36. A method for imaging an area of examination by transmitting an ultrasound beam into said area of examination and receiving signals reflected back from said area of examination using an ultrasound transducer having a multiple number of layers disposed one on top of the other; the method comprising the steps of:
   applying a signal across each one of the multiple number of layers in a transmit mode;
   isolating signals generated across at least one layer of the multiple number of layers in a receive mode.

37. A method according to claim 36 wherein the step of isolating comprises forming an open circuit between at least the one layer and a receiver.

38. A method according to claim 36 wherein the step of isolating comprises forming a short circuit across the at least one layer.

39. A method for imaging an area of examination by transmitting an ultrasound beam into said area of examination and receiving signals reflected back from said area of examination, the method comprising the steps of:
   providing an ultrasound transducer having a multiple number of layers disposed one on top of the other;
   transmitting an ultrasound beam by applying a signal across each one of the multiple number of layers;
   receiving signals generated across the multiple number of layers used to transmit the ultrasound beam; and
   isolating signals generated across at least one layer of the multiple number of layers.

40. A method for imaging according to claim 39 wherein the step of isolating signals comprises forming a short circuit across the at least one layer.

41. A method for imaging according to claim 39 wherein the step of isolating signals comprises forming an open circuit between the at least one layer and a receiver.

42. An ultrasound system for generating an image of an object located in an area of examination, said system comprising:

a transducer probe for transmitting an ultrasound signal at a first frequency and receiving an ultrasound signal at a second harmonic frequency;
transmit circuitry for transmitting signals to a transducer probe; and
receive circuitry for processing the signals received by the transducer probe, wherein said transducer probe includes transducer elements where each transducer element is formed by a multiple number of layers of piezoelectric material disposed on each other wherein said transmit circuitry is electrically coupled to the multiple number of layers and said receive circuitry is electrically isolated from at least one layer of the multiple number of layers.

43. An ultrasound transducer comprising:
a first transducer layer physically and electrically coupled to a transceiver when the transceiver is in a transmit mode and a receive mode; and
a second transducer layer disposed on the first layer, said second layer being physically coupled to the transceiver when the transceiver is in the transmit and receive mode but electrically decoupled from the transceiver when the transceiver is in the receive mode.

44. An ultrasound transducer according to claim 43 further comprising a diode coupled between the second layer and the transceiver to electrically decouple the second layer from the transceiver when the transceiver is in the receive mode.

45. An ultrasound transducer according to claim 43 further comprising a transistor coupled between the second layer and the transceiver to electrically decouple the second layer from the transceiver when the transceiver is in the receive mode.

46. An ultrasound transducer according to claim 43 further comprising a pair of diodes connected in parallel coupled between the second layer and the transceiver to electrically decouple the second layer from the transceiver when the transceiver is in the receive mode.

47. An ultrasound transducer comprising:
a first transducer layer physically coupled to a transceiver;
a second transducer layer physically coupled to the transceiver; and
means for electrically coupling the first and second layers to the transceiver during transmit mode and electrically decoupling the first and second layer from the transceiver during receive mode.

48. An ultrasound transducer according to claim 47 wherein the means for electrically coupling and decoupling comprises a diode coupled between the second layer and the transceiver.

49. An ultrasound transducer according to claim 47 wherein the means for electrically coupling and decoupling comprises a transistor coupled between the second layer and the transceiver.

50. An ultrasound transducer according to claim 47 wherein the means for electrically coupling and decoupling comprises a pair of diodes connected in parallel coupled between the second layer and the transceiver.

51. An ultrasound transducer comprising:
a first transducer layer having a first electrode and a second electrode wherein the first and second electrodes are located on opposite surfaces of the first layer wherein the first electrode is disposed on a backing block;
a second transducer layer having a third electrode and a fourth electrode wherein the third and fourth electrodes are located on opposite surfaces of the second layer wherein the second layer is disposed on the first layer so that the second and third electrodes are in contact with one another and coupled to ground;

a transceiver physically coupled to the first and fourth electrodes; and means for electrically coupling the first and fourth electrodes to the transceiver during transmit mode and electrically decoupling the first electrode from the transceiver during receive mode.

52. An ultrasound transducer according to claim 51 wherein the means for electrically coupling and decoupling comprises a diode coupled between the first and fourth electrodes.

53. An ultrasound transducer according to claim 51 wherein the means for electrically coupling and decoupling comprises a pair of diodes coupled in parallel between the first and fourth electrodes.

54. An ultrasound transducer according to claim 51 wherein the means for electrically coupling and decoupling comprises a transistor coupled between the first and fourth electrodes.

55. An ultrasound transducer according to claim 51 wherein the means for electrically coupling and decoupling comprises a transistor coupled between the first electrode and ground and a diode coupled between the first and fourth electrodes.

56. An ultrasound transducer according to claim 51 wherein the second and third electrodes are one common electrode.

57. An ultrasound transducer comprising:

a transducer probe having a transducer element comprising a first layer and a second layer disposed on the first layer;

a common electrical conductor coupled to the first and second layers of the transducer element wherein said common electrical conductor will be coupled to a transmit and receive beamformer when the transducer is coupled to an ultrasound system; and means for isolating electrical signals developed across said second layer when the transducer is in use.

58. An ultrasound transducer according to claim 57 wherein the means for isolating is located in the transducer probe.

59. An ultrasound transducer according to claim 57 wherein the common electrical conductor is a cable.

60. An ultrasound transducer comprising:

a transducer probe having a transducer element comprising a first layer and a second layer disposed on the first layer;

a common electrical conductor coupled to the first and second layers of the transducer element; and a switch coupled between said common electrical conductor and the second layer wherein the switch couples electrical signals to the second electrode during a transmit mode of operation of an ultrasound system and isolates electrical signals developed across the second electrode during a receive mode of operation when the transducer probe is coupled to an ultrasound system.

61. An ultrasound transducer according to claim 60 wherein the switch is a diode.

62. An ultrasound transducer according to claim 60 wherein the switch is located in the transducer probe.

63. An ultrasound transducer probe for transmitting an ultrasound beam into an area of examination and receiving signals reflected from said area of examination when the probe is coupled to an ultrasound system, the probe comprising:

a first layer of transducer material having a first electrode on one side of said first layer and a second electrode on an opposite side of said first layer;

a second layer of transducer material disposed on said first layer, said second layer having a third electrode on one side of said second layer and a fourth electrode on an opposite side of said second layer;

a common electrical conductor to the first, second, third and fourth electrodes for transmitting electrical signals to said first and second layers and receiving electrical signals from said first and second layers; and means for isolating electrical signals received from said second layer.

64. An ultrasound transducer comprising:

a transducer probe having a transducer element comprising a first layer and a second layer; and a common electrical conductor coupled to the transducer probe when the transducer probe is in use wherein the common electrical conductor is electrically coupled to both the first and the second layers when the transducer probe is operated in a transmit mode and the common electrical conductor is electrically decoupled from the second layer when the transducer probe is operated in a receive mode.

65. An ultrasound transducer according to claim 64 wherein a switch is located in the transducer probe and the switch is active when the transducer probe is operated in the receive mode to electrically decouple the second layer from the common electrical conductor.

66. An ultrasound transducer according to claim 65 wherein the switch is a diode.

67. An ultrasound transducer according to claim 65 wherein the switch is a transistor.

* * * * *